United States Patent [19]

Braden et al.

[11] Patent Number: 5,468,787
[45] Date of Patent: Nov. 21, 1995

[54] BIOMATERIALS FOR TISSUE REPAIR

[76] Inventors: Michael Braden, 68 Cravells Road, Harpenden, Herts AL5 1BD, England; Sandra Downes, 74 Mill Way, Bushey, Watford, Herts WD2 2AG, England; Mangala P. Patel, 45 Ellesmere Avenue, Mill Hill, London NW7 3EX, England; Kenneth W. M. Davy, 11 Chapel Gardens, Lindford, Nr Bordon, Hants GU35 OTA, England

[21] Appl. No.: 244,322
[22] PCT Filed: Nov. 17, 1992
[86] PCT No.: PCT/GB92/02128
§ 371 Date: Jun. 16, 1994
§ 102(e) Date: Jun. 16, 1994
[87] PCT Pub. No.: WO93/09819
PCT Pub. Date: May 27, 1993

[30] Foreign Application Priority Data

Nov. 18, 1991 [GB] United Kingdom .................. 9124487

[51] Int. Cl.⁶ .......................... A61L 25/00; A61K 37/36; C08L 33/14
[52] U.S. Cl. ................ 523/113; 604/51; 604/56; 523/115; 523/116; 128/898; 524/531; 424/422; 424/78.32
[58] Field of Search .............. 604/51, 56; 128/898; 523/113, 115, 116; 524/531; 424/422, 78.32

[56] References Cited

U.S. PATENT DOCUMENTS 4,820,744   4/1989   Kubota et al. ..................... 523/116

FOREIGN PATENT DOCUMENTS 0088845    9/1983   European Pat. Off. .
0032249    7/1981   United Kingdom .
WO89/03695 5/1989   WIPO .

OTHER PUBLICATIONS

Patel, M. P. et al "Heterocyclic methacrylates..." Chemical Abstracts, vol. 116, No. 24, 27 Jan. 1992.

Primary Examiner—Paul R. Michl
Assistant Examiner—Andrew E. C. Merriam
Attorney, Agent, or Firm—Nixon & Vanderhye

[57] ABSTRACT

A curable composition of a monomeric heterocyclic acrylic or methacrylic ester and an acrylate or methacrylate polymer is used to promote tissue repair, especially cartilage repair.

8 Claims, 6 Drawing Sheets

BIOMATERIALS FOR TISSUE REPAIR

BACKGROUND OF THE INVENTION

This invention relates to the use of biomaterials for tissue repair and is particularly concerned with the use of physiologically acceptable polymeric materials in such tissue repair, especially cartilage repair.

The use of physiologically acceptable polymeric materials in the preparation of biomedical appliances such as hearing aids, artificial eyes and dentures is well Known, as is the use of polymeric materials as bone cements in the field of orthopaedics. Such polymeric materials are often used in the form of a curable composition which is initially in a fluid, semi-liquid, dough-like or other mouldable form, but which cures or hardens at the temperature of use to form a strong solid of physical properties dependent on the use to which it is being put. Examples of such curable compositions are to be found in International Patent Application No. WO89/03695 and GB Patent 2 107 341 which disclose the use of curable compositions comprising a powdered methacrylate polymer mixed with a methacrylate monomer. For such applications as the preparation of hearing aids, artificial eyes and dentures which require dimensional accuracy, it is important to provide compositions of low linear curing shrinkage and GB Patent 2 107 341 is directed to such an aim. For use as bone cement it is important to prevent subsequent failure at the bone-cement interface and, to this end, WO89/03695 discloses the inclusion of a cell growth stimulant such as human growth hormone so as to increase the rate of healing of, for example, a bone fracture and give a joint of increased strength. The emphasis in the previous use of these curable compositions has therefore been directed to attaining bonding strength and/or material strength and dimensional stability dependent on the intended use.

DESCRIPTION OF THE INVENTION

Surprisingly, it has been found that certain curable compositions comprising a methacrylate polymer mixed with a suitable unsaturated monomer can be employed to promote tissue repair, with or without the addition of cell growth stimulants such as human growth hormone. Even more surprisingly, it has been found that such compositions can be employed to promote cartilage repair.

Cartilage, which differs from bone in construction, has previously been considered substantially non-repairable. Attempts to repair cartilage currently include the introduction of carbon fibres behind the cartilage; however such carbon fibres are brittle and, while a fibrous tissue forms in the implanted area, the resulting growth is not that of true cartilage composed of chondrocytes expressing their normal phenotype and producing their own matrix components. Implantation of cartilage components and hydrogel compositions have also been tried with limited success. There is therefore a great need for a breakthrough in the treatment of cartilage defects.

The present invention comprises the use of a moromet/polymer mixture in the preparation of a curable composition for introduction to a site requiring tissue repair in a human or animal body in order to promote said tissue repair, the monomer component being selected from monomeric esters of general formula I $$CH_2=C(R)-COO(CH_2)_m X \quad (I)$$

wherein R is a hydrogen atom or a methyl group, m is 0, 1 or 2, and X is a 3 to 6 membered heterocyclic ring and the polymer component is selected from acrylate and methacrylate polymers and copolymers thereof. Preferably X is an oxygen containing heterocycle.

According to a further aspect of the invention there is provided a process for the promotion of tissue repair comprising introducing to a site requiring tissue repair in a human or animal body, a curable composition comprising a monomer component selected from monomeric esters of general formula I above and a polymer component selected from acrylate and methacrylate polymers and copolymers thereof and causing or allowing the composition to cure in contact with the site.

The monomeric ester component is preferably selected from methacrylates where X is a heterocyclic group of formula

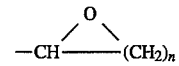

where n is 1, 2, 3 or 4. Tetrahydrofurfuryl methacrylate (R=CH$_3$, m=1, n=3) is particularly preferred. These monomers may be admixed with other monomers to control hydrophilicity, for example hydroxyethyl methacrylate to increase hydrophilicity or isobornyl methacrylate to decrease hydrophilicity. The polymer component is preferably a methacrylate polymer, preferably poly(ethyl methacrylate), but other polymers such as poly(methyl methacrylate), poly(hydroxyethyl methacrylate), or poly(tetrahydrofurfuryl methacrylate) may be employed as well as copolymers thereof. The copolymer component may be selected to control hydrophilicity.

The composition is suitably in the form of a mixture of finely divided solid polymer, suitably prepared by suspension polymerisation, in liquid monomer. The composition may include initially, or have added to it at the point of use, suitable activators for the curing such as free radical catalysts, e.g. peroxide/amine initiator systems. Alternatively, photoinitiators could be used, e.g. camphor quinine/tertiary amine systems well Known in the art. Additional additives such as stabilisers and fillers and x-ray opacifying agents may be present. These include, for example, quinone type inhibitors in the monomer, and/or inorganic fillers to increase hardness and reduce polymerisation shrinkage. In particular, hydroxyapatite may be used for this purpose and to improve biocompatibility. In addition, antibiotic components such as gentamicin may be added in order to avoid infection. Other possible therapeutic additives include anti inflammatory drugs, hydrocortisones, dexamethasone and drugs for the treatment of osteoarthritis when promoting tissue repair in a diseased joint. Other examples are antifungal agents and antimicrobial agents. Other possible additives include porosogens such as collagen or dextran to increase the porosity of the material or materials which function as protein carriers.

A particularly preferred additive is a cell growth stimulant such as those described in WO89/03695, and in particular, human growth hormone. Other growth factors such as TGF-↑, IGF I, IGF-↑, FDGF and FGF may be used.

The ratio of monomer to polymer component can vary dependent on the reaction time required and the consistency of composition required initially. Suitably the ratio of polymer to monomer is from 1:1 to 2:1 by weight, preferably 1.25:1 to 1.75:1. The curing should desirably occur at body temperature and curing is desirably effected over a period of 5 to 20 minutes, preferably 10 to 15 minutes. The use of such compositions as biomaterials in dental, aural and opthalmic fields is described in GB 2 107 341.

It is postulated that the ability of such cured compositions to promote tissue repair results from their ability to absorb water to an extent which allows absorption of tissue fluid from the area requiring repair, while swelling in the tissue to provide good bonding conditions. It is postulated that, in order to be well suited for use in accordance with the present invention, the biopolymer composition when cured should have a water uptake in the region of 5 to 30% w/w over a period of six months to 2 years. It is also recognised that the low shrinkage properties of such biopolymers combined with the slight swelling occurring with water uptake give materials which bond firmly in use, for example in cartilage, and are not readily dislodged.

The monomer/polymer mixture of the invention is preferably used to manufacture a composition intended for introduction at, or adjacent to damaged cartilage to promote cartilage repair. It has been found advantageous to apply the composition below, preferably slightly below the surface of the subchondral bone in order to optimize the formation of a new cartilage layer. However, the repair of other damaged tissue such as bone, epithelial and endothelial tissue is also contemplated within the scope of the invention, as a result of enhanced cell proliferation and differentiation in a biologically advantageous matrix.

BRIEF DESCRIPTION OF THE DRAWINGS

The invention will now be further described by way of example, with reference to the accompanying drawings, in which.

EXAMPLE 1

A curable monomer/polymer composition was prepared by mixing poly(ethyl methacrylate) in powdered form <obtained from Bonar Polymers Ltd., Ref. T/S 1249/4, Newton Aycliffe, Co. Durham, U.K. and of molecular weight about 250,000) (10 g) with tetrahydro- furfuryl methacrylate monomer <obtained from Rohm Chemie, Darmstadt, Germany) (5 ml) containing 2.5% v/v of N,N'-dimethyl-p-toluidene as activator. The polymer component contained 8% w/w $BaSO_4$ incorporated during the polymerisation process to confer radioopacity.

Human growth hormone (obtained from Novo Nordisk, Denmark) was incorporated into the material by mixing 12 IU with 10 g powder component prior to adding the monomer.

Figure 1:
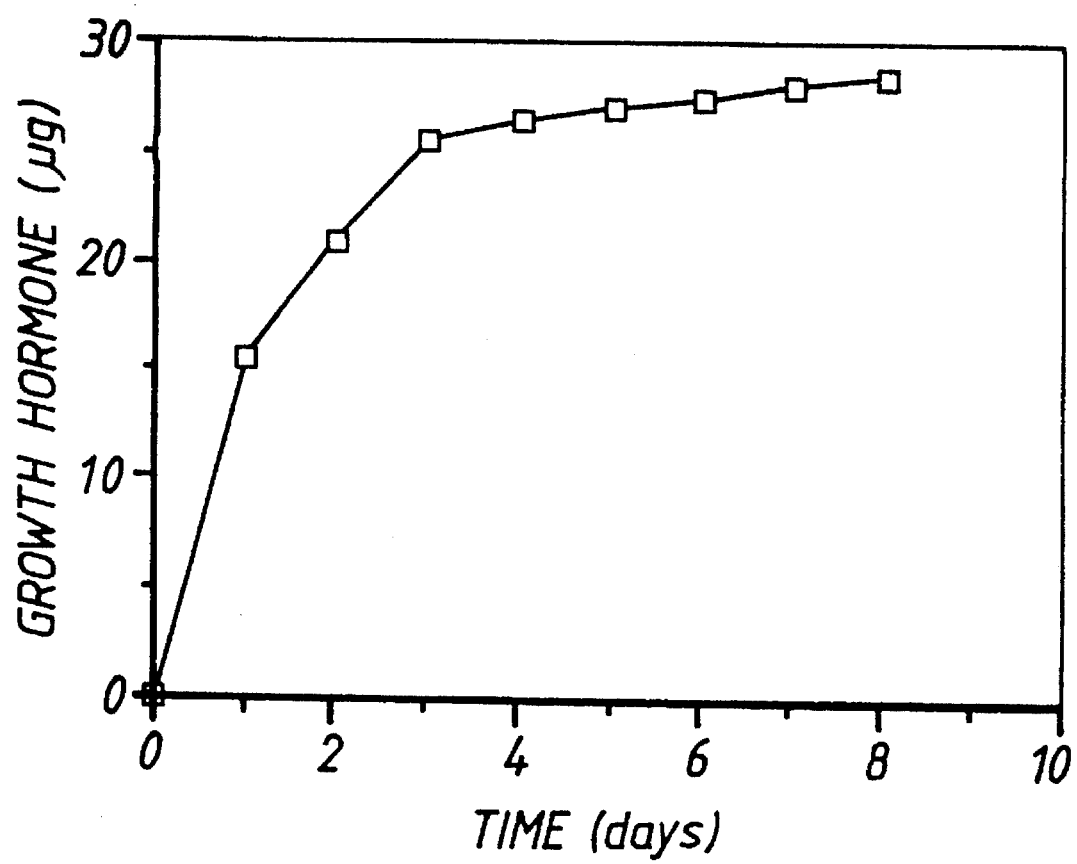
FIG. 1 shows the in vitro release of human growth hormone.
Figure 2:
FIGS. 2 through 6 show the effect of incorporating a curable monomers/polymer composition comprising growth hormone into a rabbit knee joint.
Figure 3:
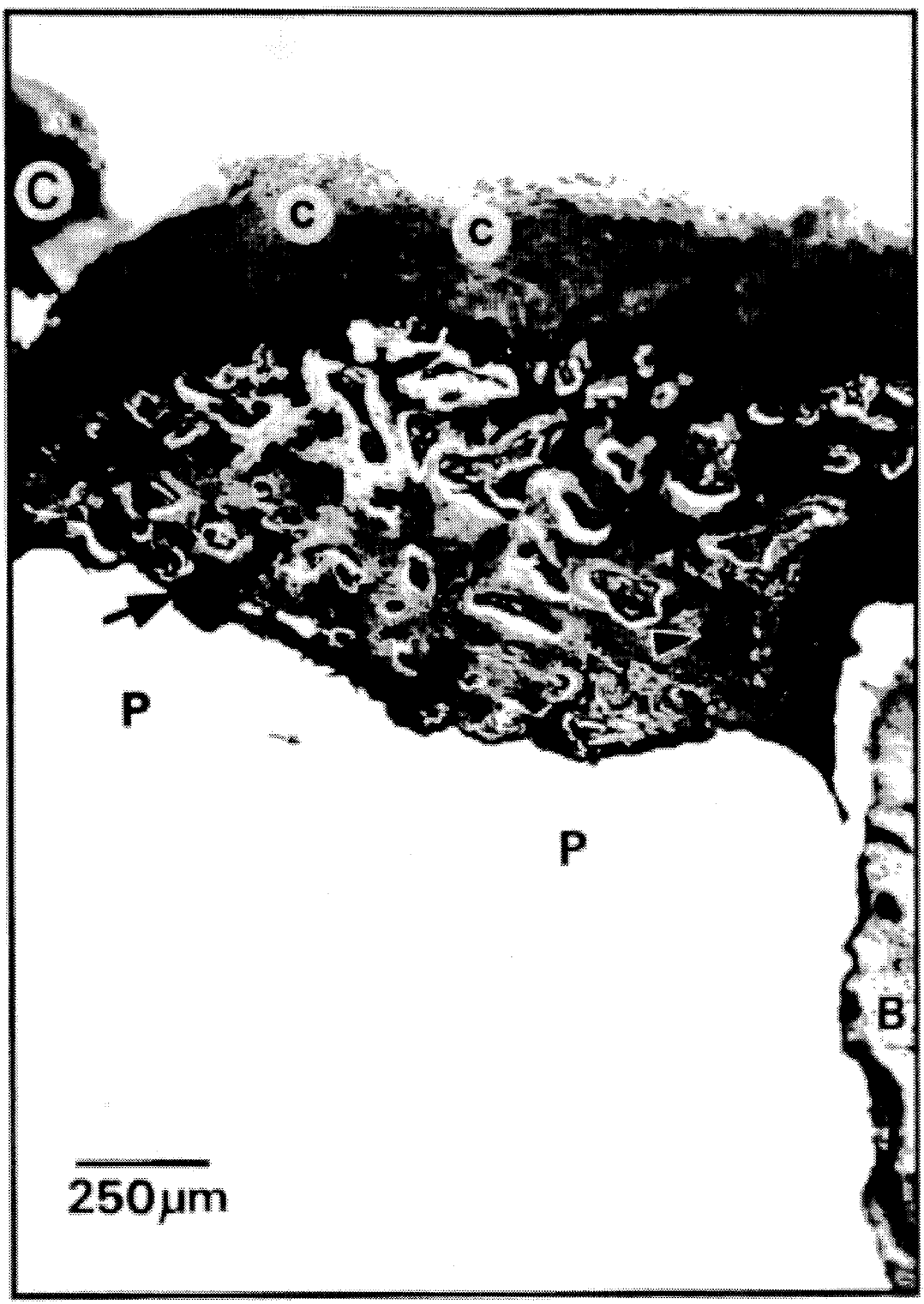
Figure 4:
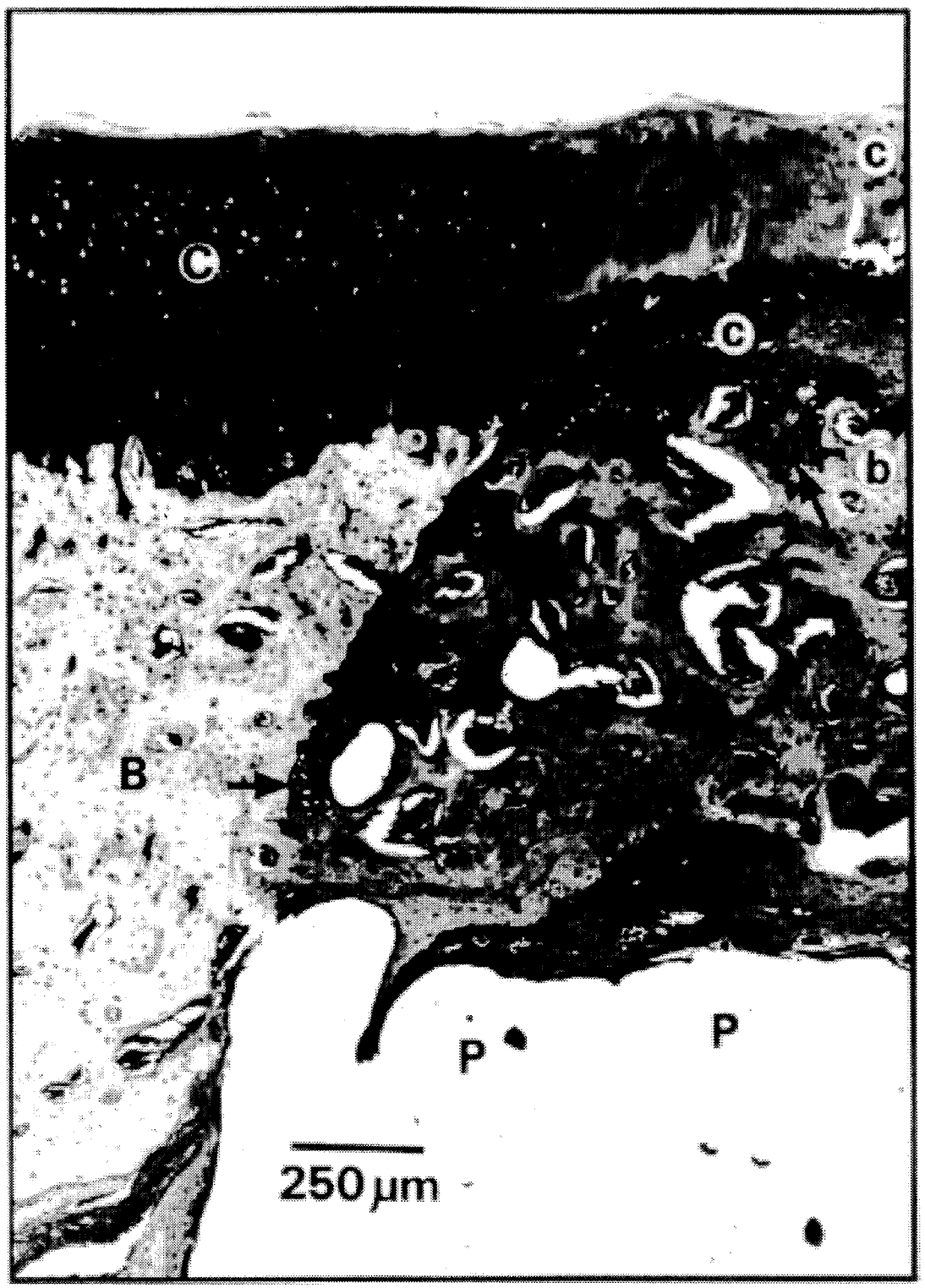
Figure 5:
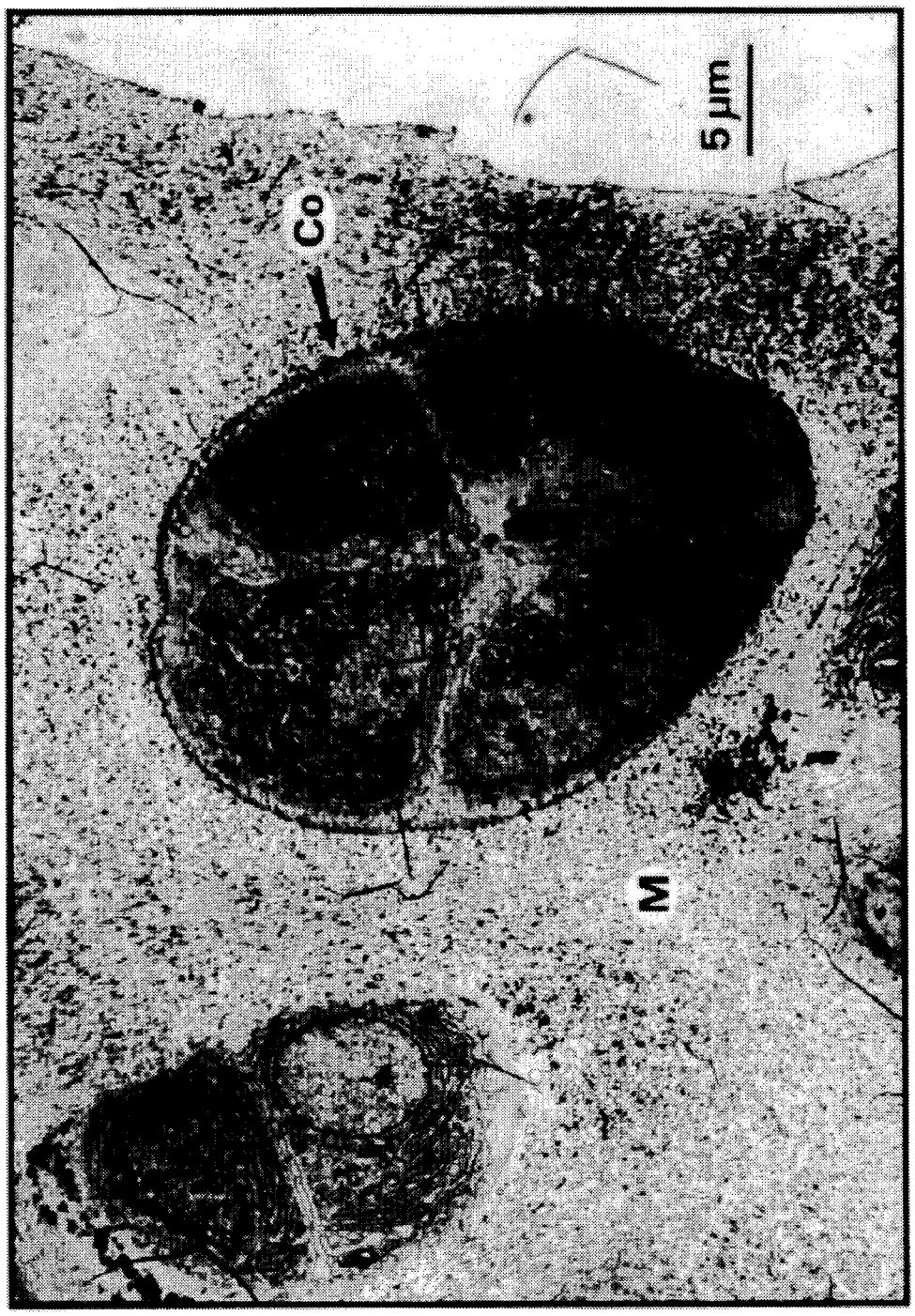
Figure 6:
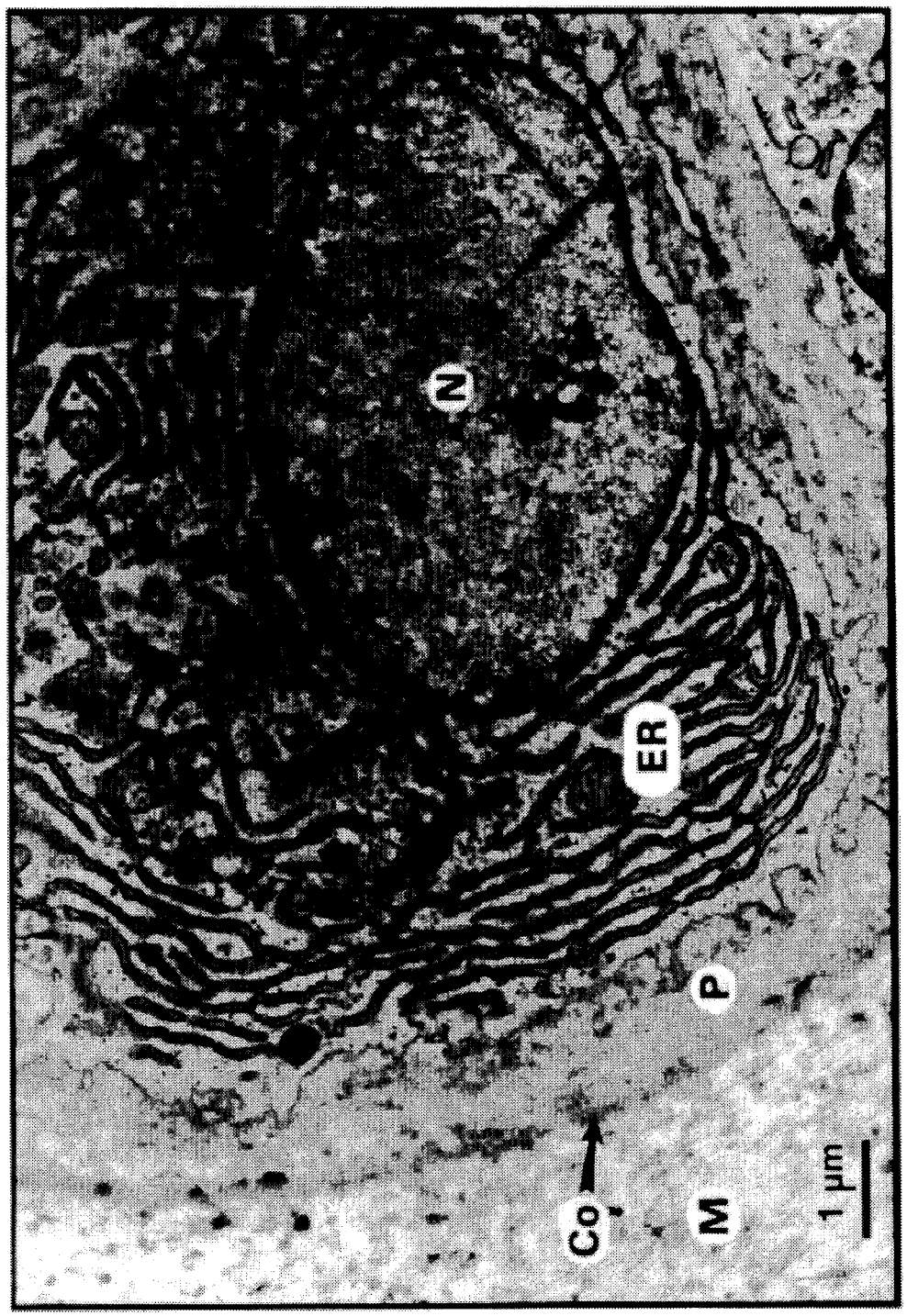

The composition was cast in discs of diameter 2 mm at a temperature of 37° C. Elution of the growth hormone was monitored by immersion of the discs in 0.1M phosphate buffered saline at 37° C. at suitable time intervals using a specific ELISA. FIG. 1 shows the in vitro release of human growth hormone.

The surface properties of the discs as cast were examined by scanning electron microscopy. This revealed that the cured polymer had a smooth surface, as compared to the rough surfaces obtained with more conventionally employed polymethyl methacrylate.

Portions of 2 ml of the curable composition prepared as above, immediately after mixing, were inserted by syringe into drilled holes in the knees of three rabbits (adult Sandy Lop, weight of least 3.5 Kg) which were then Kept unrestrained for eight months. Rapid healing and wound closure were noted and the rabbits quickly regained mobility and appetite. The tissue response at the bone-polymer interface and cartilage-polymer interface were examined. At the macroscopic level it was apparent that the cartilage defect had healed.

EXAMPLE 2

A curable composition as described in Example 1 was employed. The composition was in the form of a liquid monomer containing the dispersed polymer.

A single 3 mm diameter defect was drilled into the intercondylar notch of the articular cartilage of 18 mature Sandy Lop rabbits. Into each defect was inserted 0.15 ml of the curable composition containing human growth hormone (12 international units per 5 g polymer powder) into the subchondral bone below the area of removed cartilage. Plain curable composition without any growth hormone was inserted into a similar cartilage defect in the contralateral limb. Rabbits were sacrificed at 3,6,9 and 12 weeks and 8 months.

Histology. At each time interval, excess bone was removed from the femoral condyles before fixation in 2% paraformaldehyde and 0.5% glutaraldehyde, at 4° C., for 48 hours. Each specimen was decalcified in neutral EDTA at 4° C. prior to either low temperature (4° C.) dehydration and wax embedding, or frozen section preparation.

Cryosectioning. At each time interval decalcified specimens were frozen in cryomountant using liquid nitrogen. These were cryostat sectioned at −20° C., whilst the polymer was held in place with double-sided sellotape, sections were then mounted on glass slides and stained.

Immunolocalisation of collagen type II, chondroitin 4 sulphate and chondroitin 6 sulphate. Dewaxed sections were chondroitinase digested (0.25 iu/ml) for one hour at 38° C. to reveal the epitopes before immunolocalisation. Selected primary monoclonal antibodies were used individually and a rhodamine conjugated anti-murine serum was applied to each section, after appropriate wash steps between stages. Non-immune mouse serum was applied as control to all immunolocalisations and pre-absorbed anti-collagen type II monoclonal was used as an extra control for the localisation of collagen type II which is specific to cartilage.

Electron Microscopy. At each time Interval, excess bone was removed from the femoral condyles before fine trimming to the area of defect repair, before fixation with 2.5% glutaraldehyde in sodium cacodylate buffer at 4° C., for a minimum 48 hours. Specimens were post fixed in 1% osmium tetroxide for 2 hours before dehydration through a methanol series into propylene oxide and embedding in Spurr's resin.

The results observed were as follows:

Macroscopic findings. None of the rabbits died, nor was there any evidence of infection. The rabbits were housed in group pens which allowed freedom of movement i.e. running, jumping, standing on hind legs. The animals showed no sign of discomfort and all enjoyed full mobility. In most rabbits the knee joints showed a white glistening cartilage-like tissue resembling the normal surrounding articular cartilage. There appeared to be a good overgrowth of cartilage over the polymer within the defect. In three rabbit knees the tissue covering was incomplete; histological observations revealed that the polymer had been set above the level of the subchondral bone in the cartilage defect. Since cartilage cannot grow through the polymer, it is therefore important that the polymer is set at the right level to allow good resurfacing.

Two rabbits were kept for a longer study (eight months). The joints remained functional throughout the study period. The histology revealed that the new cartilage remained intact but the density of the matrix had still not achieved that of the original cartilage. There were still a mixed population of cells and areas of fibrous and chondrogenic regions. The subchondral bone had remodelled and in it the polymer became surrounded by very dense collagen.

Frozen sections. Cryostat sectioning allowed visualisation of the intact polymer-tissue interface, hence the extracellular matrix components of the tissue growing over the polymer three weeks after surgery were characterised. Histologically a variety of tissues were observed. Most prominent in the early stages was the observation of a highly cellular fibrous tissue. A thin layer of synovial appearance separated the new tissue covering the polymer from the intracondylar space. Bony spicules appeared to be associated with areas of new tissue immediately adjacent to the polymer surface. Above this interface the fibrous layer contained areas of rounded cells in a metachromatically stained matrix believed to be chondrogenic nodules.

Low temperature wax embedded tissue sections. Immunolocalisation of collagen type II within the cartilaginous nodules confirmed the chondrogenic phenotype of these areas of the tissue. Immunolocalisation studies also demonstrated an elaboration of chondroitin 4-sulphate and chondroitin 6-sulphate glycosaminoglycan side chains both in the fibrous tissue and in the regions of chondrogenic nodules. The varieties of cell phenotypes within the layer covering the polymer were shown histologically and by immunolocalisation of their matrix molecules during the first twelve weeks after implantation.

Transmission electron microscopy of the trans-polymer tissue layer after 8 months of implantation showed the rounded appearance of cells within a proteoglycan rich matrix, indicating the chondrogenic nature of the tissue. The presence of chondron at the cartilage and bone Interface was noted.

Growth hormone incorporation. It was shown that the cured polymer system was a good vehicle for the release of growth hormone. Morphological comparisons were made between the tissue covering the growth hormone and plain polymer.

FIGS. 2 to 6 illustrate the above findings as follows:

FIG. 2

After 3 weeks of Implantation a fibrous tissue layer (f) had grown over the polymer (P) surface, The polymer (P) had been inserted into a sub-chondral defect in the bone (B) below the level of the remaining cartilage (C).

Decalcified tissue embedded In wax. Section is stained with Methylene blue-Azur II.

FIG. 3

After 6 weeks of implantation two zones of repair tissue were observed. Bony spicules (b) and nodules containing chondrocytes (arrowed) are seen in the zone immediately above the polymer (P) surface. Where the defect has been made in the cartilage (C) a tissue layer similar in appearance but less organised than normal cartilage (c) has formed above the bony zone. Original bone is denoted B, and the original cartilage is denoted C.

Decalcified tissue embedded in wax. Section is stained with Methylene blue-Azur II.

FIG. 4

After 9 weeks of implantation there is more new bone (b) above the polymer (P) surface. There are nodules containing chondrocytes (arrow) in the bony layer. The new cartilage (c) is disorganised. Original bone is denoted B, and the original cartilage is denoted C.

Decalcified tissue embedded in wax. Section is stained with Methylene blue-Azur II.

FIG. 5

By transmission electron microscopy clusters of chondrocytes are seen to be contained within a collagenous basket (co). These are referred to as chondrons and are structures normally observed in the deep zones of mammalian cartilage. The normal extracellular matrix is denoted M.

FIG. 6

The cells within the chondron (Co) appear to be actively synthesising cell products indicated by the enormous amount of endoplasmic reticulum (ER). The cell nucleus is denoted N and the normal extracellular matrix is denoted M.

We claim:

1. A method of promoting repair of cartilage in a human or animal body, which comprises the steps of:

introducing to cartilage requiring repair in said body a curable monomer/polymer composition, the monomer component having the formula I

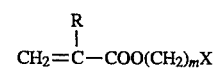

where R is a hydrogen atom or a methyl group, m is 0, 1 or 2 and X is a 3 to 6 membered heterocyclic ring and the polymer component being selected from the group consisting of acrylate and methacrylate polymers and copolymers thereof; and causing or allowing the composition to cure in contact with said cartilage and promote repair of said cartilage.

2. A method according to claim 1, wherein X in the monomer component of formula I is an oxygen-containing heterocycle.

3. A method according to claim 2, wherein the monomer component is tetrahydrofurfuryl methacrylate.

4. A method according to claim 2, wherein the polymer component is polyethylmethacrylate.

5. A method according to claim 1, wherein the curable composition has a polymer to monomer ratio of 1:1 to 2:1 by weight.

6. A method according to claim 1 in the preparation of a curable composition further comprising one or more components selected from the group consisting of antimicrobial agents, porosogens, protein carriers and cell growth stimulants.

7. A method according to claim 6, wherein a said component is human growth hormone.

8. A method according to claim 1, wherein the curable composition is introduced below the surface of the subchondral bone.

* * * * *